(12) United States Patent
Pretorius et al.

(10) Patent No.: US 12,385,904 B2
(45) Date of Patent: Aug. 12, 2025

(54) METHOD OF DETECTING INFLAMMATION

(71) Applicant: Stellenbosch University, Stellenbosch (ZA)

(72) Inventors: Etheresia Pretorius, Stellenbosch (ZA); Douglas Bruce Kell, Manchester (GB); Willem Johan Simon De Villiers, Stellenbosch (ZA)

(73) Assignee: Stellenbosch University, Stellenbosch (ZA)

( * ) Notice: Subject to any disclaimer, the term of this patent is extended or adjusted under 35 U.S.C. 154(b) by 608 days.

(21) Appl. No.: 16/763,470

(22) PCT Filed: Nov. 13, 2018

(86) PCT No.: PCT/IB2018/058903
§ 371 (c)(1),
(2) Date: May 12, 2020

(87) PCT Pub. No.: WO2019/092677
PCT Pub. Date: May 16, 2019

(65) Prior Publication Data
US 2020/0363403 A1     Nov. 19, 2020

(30) Foreign Application Priority Data
Nov. 13, 2017  (GB) .................... 1718704

(51) Int. Cl.
*G01N 3/50*        (2006.01)
*G01N 33/50*       (2006.01)
*G01N 33/564*      (2006.01)

(52) U.S. Cl.
CPC ..... *G01N 33/5091* (2013.01); *G01N 33/5008* (2013.01); *G01N 33/564* (2013.01); *G01N 2800/52* (2013.01)

(58) Field of Classification Search
CPC ........... G01N 33/5091; G01N 33/5008; G01N 33/564; G01N 33/52; G01N 33/5002; G01N 2800/52; G01N 2800/7095; G01N 2800/7047; G01N 2800/226; G01N 2800/28; G01N 2800/2871; G01N 2800/24; G01N 2800/065; G01N 2800/323
See application file for complete search history.

(56) References Cited

U.S. PATENT DOCUMENTS

2009/0202980 A1* 8/2009 Gebbink ............. C07K 16/40 530/387.3

FOREIGN PATENT DOCUMENTS

| CN | 103827671 A | 5/2014 |
| CN | 106018829 A | 10/2016 |
| CN | 106706926 A | 5/2017 |

OTHER PUBLICATIONS

Cortes-Canteli M et al. Fibrinogen and beta-amyloid association alters thrombosis and fibrinolysis: A possible contributing factor to Alzheimer's disease. Neuron, 66, 695-709. (Year: 2010).*
Kell DB and Pretorius E. Proteins behaving badly. Substoichiometric molecular control and amplification of the initiation and nature of amyloid fibril formation: lessons from and for blood clotting. Prog. Biophys. Mol. Biol. 123, 16-41; Epub Aug. 21, 2016. (Year: 2017).*
Schultz DR et al. Properties of four acute phase proteins: C-reactive protein, serum amyloid A protein, alpha1-acid glycoprotein, and fibrinogen. Seminars in Arthritis and Rheumatism, 20(3), 129-147; abstract only. (Year: 1990).*
Urieli-Shoval S et al. Expression and function of serum amyloid A, a major acute-phase protein, in normal and disease states. Curr. Opin. Hematol. 7, 64-69. (Year: 2000).*
Page MJ et al. Serum amyloid A binds to fibrin(ogen), promoting fibrin amyloid formation. Scientific Rep. 9:3102, 14 pages. (Year: 2019).*
Soric Hosman I, Kos I, Lamot L. Serum Amyloid A in Inflammatory Rheumatic Diseases: A Compendious Review of a Renowned Biomarker. Front Immunol. 2021 (Year: 2021).*
Jennewein C, Tran N, Paulus P, Ellinghaus P, Eble JA, Zacharowski K. Novel aspects of fibrin(ogen) fragments during inflammation. Mol Med. 2011 (Year: 2011).*
LeVine H 3rd. Quantification of beta-sheet amyloid fibril structures with thioflavin T. Methods Enzymol. 1999 (Year: 1999).*
Zhmurov A, Kononova O, Litvinov RI, Dima RI, Barsegov V, Weisel JW. Mechanical transition from α-helical coiled coils to β-sheets in fibrin(ogen). J Am Chem Soc. 2012 (Year: 2012).*
European Office Action issued on Mar. 28, 2022, in related European Application No. 18811360.9.
Examination Report issued on Jun. 14, 2022, in related African Regional Intellectual Property Organization (ARIPO) Application No. AP/P/2020/012362.
Tao, S. et al., "Comparison and combination of blood-based inflammatory markers with faecal occult blood tests for non-invasive colorectal cancer screening," British Journal of Cancer, (2012) vol. 106, pp. 1424-1430.
Pretorius, Etheresia et al., "Acute induction of anomalous and amyloidogenic blood clotting by molecular amplification of highly substoichiometric levels of bacterial lipopolysaccharide", Journal of the Royal Society. Interface, vol. 13(122), Sep. 1, 2016, p. 20160539, XP55903230.
Kell, Douglas B., et al., "Proteins behaving badly. Substoichiometric molecular control and amplification of the initiation and nature of amyloid fibril formation: lessons from and for blood clotting", Progress in Biophysics and Molecular Biology, vol. 123, Sep. 30, 2016, pp. 16-41, XP029891018.

(Continued)

*Primary Examiner* — Jeffrey Stucker
*Assistant Examiner* — Katrina J. Campbell
(74) *Attorney, Agent, or Firm* — Womble Bond Dickinson (US) LLP

(57) ABSTRACT

A method of detecting inflammation in a subject is provided. The method comprises determining a quantity of amyloid present in fibrin(ogen) protein in a blood sample obtained from the subject, and assigning a level of inflammation in the subject based on the quantity of fibrin(ogen) amyloid determined. A method of determining an effect of a therapeutic treatment on a subject by comparing a pre-treatment level of inflammation with a post-treatment level is further provided.

13 Claims, 6 Drawing Sheets

(56) References Cited

OTHER PUBLICATIONS

Pretorius, E., et al., "Lipopolysaccharide-binding protein (LBP) reverses the amyloid state of fibrin seen in plasma of type 2 diabetics with cardiovascular co-morbidities," *Scientific Reports,* 2017, vol. 7(1), XP055536009.

Pretorius, E., et al., "Substantial fibrin amyloidogenesis in type 2 diabetes assessed using amyloid-selective fluorescent stains," *Cardiovascular Diabetology,* 2017, vol. 16(1), XP055536013.

Cortes-Canteli, M., et al. "Fibrin deposited in the Alzheimer's disease brain promotes neuronal degeneration," *Neurobiology of Aging,* 2014, vol. 36(2), pp. 608-617.

Shi, C., et al., "Atherosclerosis associated with dynamic inflammation changes after multifactorial intervention in short-duration type 2 diabetes: A randomized, controlled, 10-year follow-up trial," *Journal of Diabetes and its Complications,* 2017, vol. 31(8), pp. 1286-1292.

Laboratory Diagnosis Quick Reference, Wen Haixia et al., pp. 326-327, People's Military Medical Publishing House, published on Apr. 30, 2009.

* cited by examiner

METHOD OF DETECTING INFLAMMATION

CROSS-REFERENCE TO RELATED APPLICATIONS

This application is a national stage filing under 35 U.S.C. § 371 of PCT/IB2018/058903, filed Nov. 13, 2018, which International Application was published by the International Bureau in English on May 16, 2019, as WO 2019/092677, and which application claims priority from United Kingdom Application No. 1718704.8, filed on Nov. 13, 2017, which applications are hereby incorporated by reference in their entirety in this application.

FIELD OF THE INVENTION

This invention relates to methods of detecting inflammation, more particularly, methods of detecting early stage inflammation by measuring levels of amyloid in a subject's blood.

BACKGROUND TO THE INVENTION

The global disease burden is continuing to shift away from communicable diseases to non-communicable diseases such as diabetes, atherosclerosis, Alzheimer's disease, cardiovascular disease and cancer—all of which are linked to chronic low-grade inflammation. Furthermore, about 80% of people dying from these diseases now live in the developing world, which holds a particular danger for health systems of developing countries which are already under-resourced and over-stretched. It is thus essential to investigate possible markers which link inflammation to these diseases and to develop low cost methods of early detection.

Amyloids are one class of markers that have been implicated in a number of inflammatory conditions. These conditions, referred to as amyloidogenic diseases, are characterised by the formation of amyloid plaques or amyloid deposits in the body. The term amyloid refers to a highly ordered and insoluble type of protein that forms as the result of a normally soluble protein aggregating via a self-association process. In the body, this process is linked to a breakdown in the systems that ensure efficient protein synthesis and folding. Amyloid deposits can be cerebral (e.g. Alzheimer's disease and Huntington's disease), or peripheral (e.g. light chain amyloidosis and type 2 diabetes). Amyloids can affect any organ or tissue but the kidneys, pancreas, liver, spleen, nervous tissue and heart constitute the major sites of deposition in patients with peripheral amyloidosis.

Several pro-inflammatory gene products have been identified as inducers of amyloid formation, one example being serum amyloid A (SAA). SAA is a generic term for a family of acute phase proteins synthesised by the liver which are mainly regulated by inflammation associated cytokine-peptide hormone signals. Inflammation resulting from cancer, cardiovascular disease, rheumatoid arthritis, bacterial infection, and tissue damage, may cause SAA levels to rise 1000-fold. It may therefore be advantageous to measure levels of SAA in order to determine a degree of inflammation in a subject. Currently, SAA levels can be detected using enzyme-linked immunosorbent assays (ELISA) and mass spectrometry (MS). However, these methods are poorly sensitive, extremely expensive and time-consuming, which may limit their application, particularly in under resourced clinical contexts. Furthermore, due to their insensitivity, these methods may only be capable of detecting SAA levels in advanced disease states where SAA levels are considerably elevated. There is therefore room for new methods of detecting SAA levels in subjects at a higher degree of sensitivity than previously available methods.

A problem that is encountered in the field of therapy of amyloid-related and other inflammatory disorders is an inability to detect or quantify amyloid formation at an early stage of disease progression. To date, no satisfactory method has been developed by which it is possible to obtain rapid, quantitative, detection of low levels of amyloid in patients suffering from amyloid-associated conditions. Consequently, it is difficult to accurately monitor patient responses to therapy. A need exists for a method by which low levels of inflammation may be detected in such patients.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with a first aspect of the invention, there is provided a method of detecting inflammation in a subject, the method comprising determining a quantity of amyloid present in fibrin(ogen) protein in a blood sample obtained from the subject, and assigning a level of inflammation in the subject based on the quantity of fibrin(ogen) amyloid determined.

The quantity of fibrin(ogen) amyloid may be determined by contacting the blood sample with an amyloid-binding fluorescent marker, allowing amyloid in the sample to bind to the marker, measuring fluorescence emitted upon binding of the amyloid to the marker, and determining a quantity of amyloid based on the measured fluorescence.

The quantity of amyloid may be determined by comparing the measured fluorescence to a reference. The reference may be one or more predetermined values, a chart or a graph.

The subject may be diagnosed as having inflammation when the quantity of fibrin(ogen) amyloid in the blood sample is greater than a threshold level. The threshold fibrin(ogen) amyloid level may be 2, 3, 4, 5, 6, 7, 8, 9, 10, 20, 30, 40, 50, 60, 70, 80, 90, 100, 200, 300, 400, 500, 600, 700, 800, 900 or 1000 times greater than a blood level of fibrin(ogen) amyloid in a healthy subject.

The quantity of fibrin(ogen) amyloid may be associated with a level of serum amyloid A (SAA), dysregulated cytokines and/or inflammogens in the blood sample, and the level (concentration) of these molecules may correspond to a level of inflammation in the subject.

The subject may be diagnosed as having inflammation when the level of SAA in the blood sample is greater than a threshold level. The threshold level may be 2, 3, 4, 5, 6, 7, 8, 9, 10, 20, 30, 40, 50, 60, 70, 80, 90, 100, 200, 300, 400, 500, 600, 700, 800, 900 or 1000 times greater than a blood level of SAA in a healthy subject, which may be any value between 30 and 30,000 micrograms/ml, such as 30, 40, 50, 60, 70, 80, 90, 100, 200, 300, 400, 500, 600, 700, 800, 900, 1000, 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000 or 30000 micrograms/ml. The threshold level may be provided as a range of values, which may be a range between 30 and 30,000 micrograms/ml.

The inflammation may be early stage inflammation and may indicate a disease state or a pre-disease state in the subject. The disease may be selected from hypercoagulation, cancer, Alzheimer's disease, Parkinson's disease, diabetes mellitus (type I or type II), Huntington's disease, rheumatoid arthritis, atherosclerosis, amyloidosis, familial amyloid polyneuropathy, familial renal amyloidosis, haemodialysis-associated amyloidosis, cerebral amyloid angiopathy, amyloid light-chain (AL) amyloidosis, inclusion body myositis, giant cell arthritis, coronary heart disease, Behçet's disease, sickle cell anaemia, immune thrombocytopaenic purpura, human immunodeficiency virus (HIV), stroke, pre-eclampsia, inflammation-associated thrombosis, inflammatory bowel disease and Crohn's disease.

The disease may be cancer and the cancer may be pre-cancer or early stage cancer.

The subject may have no symptoms of inflammation or disease.

The fluorescence marker may be selected from Thioflavin T, NIAD-4, a luminescent conjugated oligothiophene (LCO) and Congo red.

The fluorescence may be measured by a spectrophotometer, a diode array detector or a fluorescence detector. The fluorescence may be measured by confocal microscopy and quantified by image processing software. The detected fluorescence may be compared to a reference fluorescence value in order to determine a level of fibrin(ogen) amyloid in the sample.

The blood sample may be whole blood or blood plasma.

In accordance with a second aspect of the invention, there is provided a method of detecting inflammation in a subject, the method comprising determining a quantity of serum amyloid A (SAA) in a blood sample obtained from the subject by measuring a quantity of amyloid present in fibrin(ogen) protein in the blood sample, and assigning a level of inflammation in the subject based on the quantity of SAA.

The amount of amyloid may be measured by contacting the blood sample with an amyloid-binding fluorescent marker, allowing amyloid in the sample to bind to the marker, measuring fluorescence emitted upon binding of the amyloid to the marker, and assigning an amount of amyloid based on the measured fluorescence.

The quantity of SAA may be determined by comparing the amount of amyloid to a reference. The reference may be one or more predetermined values, a chart or a graph.

The inflammation may be early stage inflammation. The subject may be diagnosed as having early stage inflammation when the quantity of SAA in the blood sample is between 30 and 30,000 micrograms/ml.

The early stage inflammation may indicate a disease state or a pre-disease state in the subject. The disease may be selected from the group consisting of hypercoagulation, cancer, Alzheimer's disease, Parkinson's disease, diabetes mellitus (type I or type II), Huntington's disease, rheumatoid arthritis, atherosclerosis, amyloidosis, familial amyloid polyneuropathy, familial renal amyloidosis, haemodialysis-associated amyloidosis, cerebral amyloid angiopathy, amyloid light-chain (AL) amyloidosis, inclusion body myositis, giant cell arthritis, coronary heart disease, Behçet's disease, sickle cell anaemia, immune thrombocytopaenic purpura, human immunodeficiency virus (HIV), stroke, pre-eclampsia, inflammation-associated thrombosis, inflammatory bowel disease and Crohn's disease. The disease may be cancer and the cancer may be pre-cancer or early stage cancer.

The disease, fluorescence marker, and fluorescence measurement may be as defined above.

The detected fluorescence may be compared to a standard curve of predetermined fluorescence values having associated SAA levels in order to determine a level of SAA in the sample.

In accordance with a third aspect of the invention, there is provided a method of determining an effect of a therapeutic treatment on a subject, the method comprising: detecting inflammation in the subject according to the methods described above before the therapeutic treatment to obtain a pre-treatment level of inflammation; detecting inflammation in the subject according to the methods described above after the therapeutic treatment to obtain a post-treatment level of inflammation; and comparing the pre-treatment and post-treatment levels of inflammation to determine the effect of the treatment.

The method may further comprise obtaining a plurality of post-treatment levels of inflammation, each of which may be obtained at spaced apart time intervals post-treatment, to monitor the effect of the treatment over time.

The treatment may be determined to be successful if the post-treatment level of inflammation is lower than the pre-treatment level of inflammation.

DETAILED DESCRIPTION OF THE INVENTION

Figure 1:
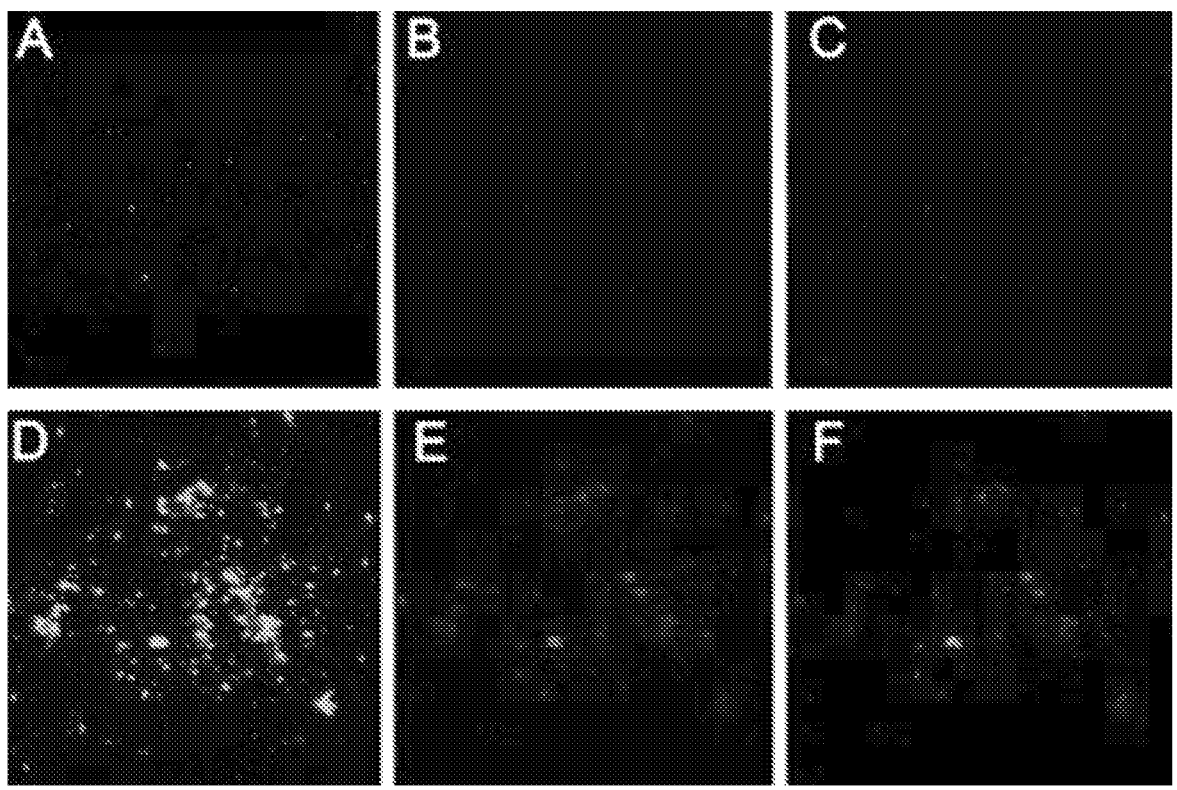
FIG. 1 is a series of confocal images of clotted platelet poor plasma (PPP) in the presence of Thioflavin T (ThT), Amytracker® 480 and Amytracker® 680: First column—Amytracker® 480; second column—Amytracker® 680; third column—ThT. A to C) healthy blood; D to F) inflamed blood.

The present invention provides a convenient, non-invasive method of detecting inflammation, particularly early stage inflammation, in a subject. The invention further provides a means of monitoring the regression, progression or treatment of an inflammatory disease and assessing the effect of therapeutic agents and treatment regimens.

The method comprises determining a quantity of amyloid present in fibrin(ogen) protein in a blood sample obtained from the subject, and assigning a level of inflammation in the subject based on the quantity of fibrin(ogen) amyloid determined. Amyloid fibrin(ogen) structure is significantly upregulated in all inflammatory conditions, when compared to fibrin(ogen) structure in healthy individuals. The fibrin(ogen) amyloid comprises fibrin(ogen) protein which has incorrectly folded or is otherwise in an anomalous state. The proportion of fibrin(ogen) present as amyloid can be correlated with a degree of inflammation in the subject. High levels of inflammation correspond with high levels of amyloid and low levels of inflammation with low levels of amyloid.

The present method can aid in the early detection of the presence of inflammation associated with inflammatory diseases, assist in determining the prognosis, define the therapeutic options, and enable a rational evaluation of therapeutic response, as reducing inflammation will result in a reduction of circulating dysregulated inflammatory markers, which is the cause of such protein changes resulting in anomalous amyloid formation in fibrin(ogen).

The term "fibrin(ogen)" as used herein is understood to refer to "fibrinogen and/or fibrin", as is commonly known in the art.

The quantity of fibrin(ogen) amyloid can be determined by contacting the blood sample with an amyloid-binding fluorescent marker, allowing amyloid in the sample to bind to the marker, measuring fluorescence emitted upon binding of the amyloid to the marker, and assigning a quantity of amyloid based on the measured fluorescence. Thrombin may be added to the sample to induce fibrin(ogen) formation and blood clotting.

The quantity of amyloid can be determined by comparing the amount of fluorescence to a reference. The reference may be one or more predetermined values, such as a value of fluorescence previously obtained from the subject or from other subjects. Each predetermined value can be associated with a quantity of amyloid, from which the quantity of amyloid determined by the method can be derived. Alternatively the reference can be a chart or a graph comprising levels of fluorescence or inflammation (or values derived therefrom) and associated amyloid or fluorescence quantities from which the quantity of amyloid determined by the method can be derived. In an exemplary embodiment, the reference can be a predetermined value on a standard curve which correlates amount of fluorescence with quantity of amyloid.

The subject can be diagnosed as having inflammation when the quantity of amyloid in the blood sample is greater than a threshold level. The threshold fibrin(ogen) amyloid level can be 2, 3, 4, 5, 6, 7, 8, 9, 10, 20, 30, 40, 50, 60, 70, 80, 90, 100, 200, 300, 400, 500, 600, 700, 800, 900 or 1000 times greater than a blood level of fibrin(ogen) amyloid in a healthy subject.

The amount of fibrin(ogen) amyloid may be associated with a level of serum amyloid A (SAA), dysregulated cytokines and/or inflammogens in circulation originating from bacterial cell wall or membrane components in the blood sample, and the level of SAA may also correspond to a level of inflammation in the subject. By associating a quantity of amyloid with a level of SAA or another suitable inflammatory marker, a degree of inflammation in the subject may be quantifiable. Equally, a quantity of SAA in the sample may be determinable from the amount of amyloid measured, for example, by comparing the amount of amyloid to a reference. The reference may be a predetermined value, a chart or a graph. A level of inflammation in the subject may be assigned based on the quantity of SAA.

The subject can be diagnosed as having inflammation when the quantity of SAA in the blood sample is greater than a threshold level. The threshold SAA level can be 2, 3, 4, 5, 6, 7, 8, 9, 10, 20, 30, 40, 50, 60, 70, 80, 90, 100, 200, 300, 400, 500, 600, 700, 800, 900 or 1000 times greater than a blood level of SAA in a healthy subject. A blood level of SAA in a healthy subject is typically from 5 to 30 micrograms/ml and the threshold level can be any value between 30 and 30,000 micrograms/ml, such as 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 11000, 12000, 13000, 14000, 15000, 16000, 17000, 18000, 19000, 20000, 21000, 22000, 23000, 24000, 25000, 26000, 27000, 28000, 29000 or 30000 micrograms/ml of SAA. The threshold level can be provided as a range of values between 30 and 30,000 µg/ml, such as 30-1000 µg/ml, 50-1000 µg/ml, 100-1000 µg/ml, 500-1000 µg/ml, 1000-2000 µg/ml, 2000-3000 µg/ml, 3000-4000 µg/ml, 4000-5000 µg/ml, 5000-6000 µg/ml, 6000-7000 µg/ml, 7000-8000 µg/ml, 8000-9000 µg/ml, 9000-10000 µg/ml, 10000-11000 µg/ml, 11000-12000 µg/ml, 12000-13000 µg/ml, 13000-14000 µg/ml, 14000-15000 µg/ml, 15000-16000 µg/ml, 16000-17000 µg/ml, 17000-18000 µg/ml, 18000-19000 µg/ml, 19000-20000 µg/ml, 20000-21000 µg/ml, 21000-22000 µg/ml, 22000-23000 µg/ml, 23000-24000 µg/ml, 24000-25000 µg/ml, 25000-26000 µg/ml, 26000-27000 µg/ml, 27000-28000 µg/ml, 28000-29000 µg/ml, 29000-30000 µg/ml, 1000-5000 µg/ml, 5000-10000 µg/ml, 10000-15000 µg/ml, 15000-20000 µg/ml, 20000-25000 µg/ml, or 25000-30,000 µg/ml.

The inflammation, which may be early stage inflammation, may indicate a disease state or a pre-disease state in the subject. The disease may be selected from hypercoagulation, cancer, Alzheimer's disease, Parkinson's disease, diabetes mellitus (type I or type II), Huntington's disease, rheumatoid arthritis, atherosclerosis, amyloidosis, familial amyloid polyneuropathy, familial renal amyloidosis, haemodialysis-associated amyloidosis, cerebral amyloid angiopathy, amyloid light-chain (AL) amyloidosis, inclusion body myositis, giant cell arthritis, coronary heart disease, Behçet's disease, sickle cell anaemia, immune thrombocytopaenic purpura, human immunodeficiency virus (HIV), stroke, pre-eclampsia, inflammation-associated thrombosis, inflammatory bowel disease and Crohn's disease. The disease may be cancer and the cancer may be pre-cancer or early stage cancer.

Association of a quantity of amyloid in the sample with a concentration of SAA may be used to diagnose a stage of inflammation in the subject. Levels of SAA less than 30 µg/ml are considered healthy and normal, levels of SAA greater than 30 μg/ml but less than 10,000 μg/ml indicate early stage inflammation, and levels of SAA greater than 10,000 μg/ml indicate the presence of advanced disease, which can include the presence of sepsis. The early stage inflammation can be indicative of cancer, which can be pre-cancer or early stage cancer. A level of SAA greater than or equal to 20,000 μg/ml can indicate advanced cancer, a level of SAA between 5,000 and 20,000 μg/ml can indicate early stage cancer, and a level of SAA less than 5000 μg/ml can indicate pre-cancer. The stages of inflammation and/or cancer may also be determined by comparing the quantity of amyloid to a reference indicating a stage of inflammation or a stage of cancer.

Pre-cancer refers to a state of disordered morphology of cells that is associated with an increased risk of cancer. It is also referred to as stage 0 cancer or cancer in situ, which is a non-invasive cancer that has not progressed to an aggressive, invasive stage. These types of cancers are located in the place in which they originated and have not spread to other tissues. Early stage cancer refers to stage 1 cancer, which is associated with a small tumour that has not grown deeply into nearby tissues. It has typically not spread to the lymph nodes or other areas on the body. Other stages of cancer which can be detected by the method include stage 2 and 3, which are characterised by larger cancers or tumours that have grown deeply into nearby tissue and which may have spread to lymph nodes but not to other parts of the body, and stage 4 in which the cancer has spread to other organs or parts of the body. Stage 4 is also referred to as advanced or metastatic cancer.

The method can be suitable for detecting early stage inflammation in a subject having no symptoms of inflammation or disease. In particular, the subject may have no detectable sepsis or infection, and in the case of cancer, may have no detectable tumours.

The term "cancer" refers to disease of skin tissues, organs, blood, and vessels, including, but not limited to, cancers of the bladder, bone or blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. The term "cancer" includes both solid tumours and blood born tumours.

The fluorescence marker used in the method can be selected from Thioflavin T, NIAD-4 [chemical name: 2-((5'-(4-hydroxyphenyl)-2,2'-bithiophen-5-yl)methylene)propanedinitrile], luminescent conjugated oligothiophenes (LCOs) and Congo red [chemical name: disodium 4-amino-3-[4-[4-(1-amino-4-sulfonato-naphthalen-2-yl)diazenylphenyl]phenyl]diazenyl-naphthalene-1-sulfonate]. The LCOs can be selected from the structures provided in Table 1 below, or a salt or free acid thereof.

TABLE 1

Chemical Structures of Selected LCOs

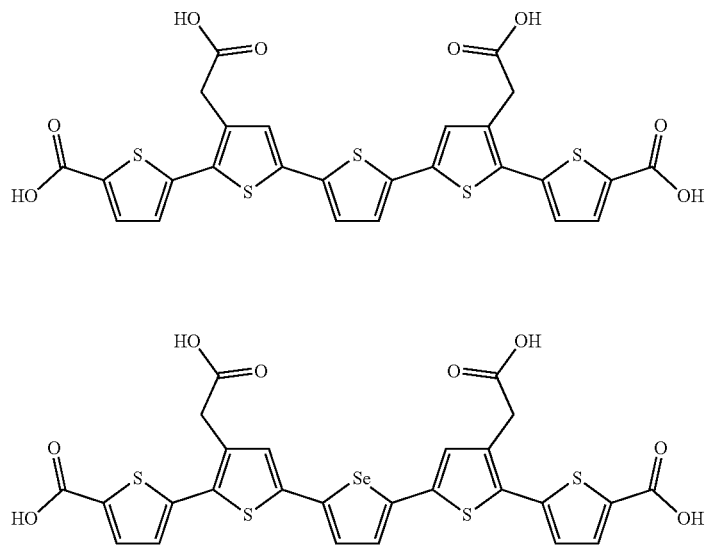

TABLE 1-continued
Chemical Structures of Selected LCOs
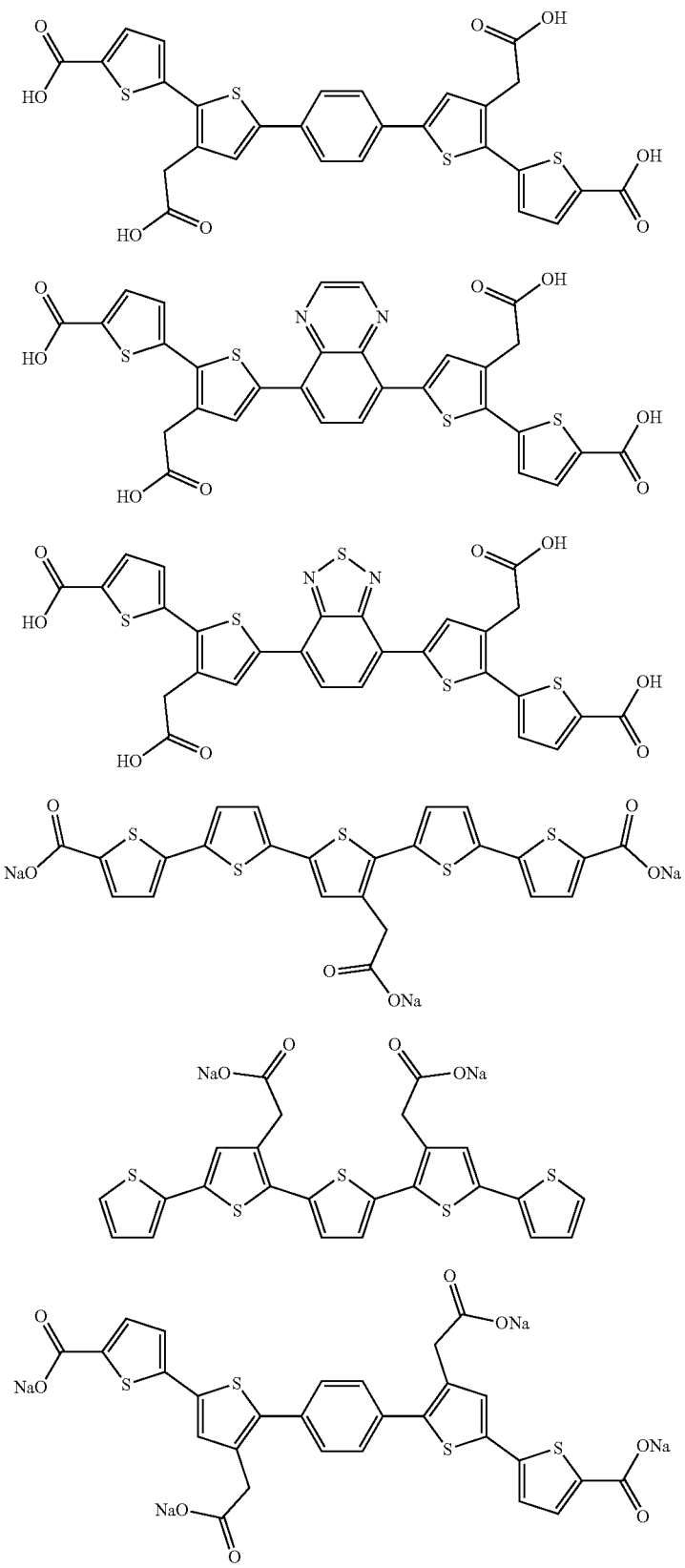

The LCO can be an Amytracker®480 having an excitation range of 405-458 nm and a detection range of 470-550 nm, an Amytracker®515 having excitation at 458 or 488 nm and a detection range of 500-650 nm, an Amytracker®545 having excitation at 458 or 488 nm and a detection range of 500-650 nm, or an Amytracker®680 having an excitation range of 530-565 nm and a detection range of 600-800 nm.

The fluorescence may be measured by a spectrophotometer, a diode array detector or a fluorescence detector. In some embodiments, the fluorescence can be measured using a confocal microscope and quantified by image processing software. In a typical embodiment, a blood sample is contacted with a fluorescence marker and the marker allowed to bind and form a conjugate with amyloid in the sample. The sample is exposed to laser excitation at a suitable wavelength to induce the marker-amyloid conjugate to fluoresce. An image is captured and fluorescence in the image quantified by suitable software, such as Zeiss ZEN or ImageJ (Fiji) software.

The blood sample can be whole blood or blood plasma. In some embodiments, whole blood can be clarified by centrifugation and the resulting platelet poor plasma used in the method. In other embodiments, whole blood can be used without clarification.

The invention extends to a method of determining an effect of a therapeutic treatment on a subject, the method comprising: detecting inflammation in the subject according to the method described above before the therapeutic treatment to obtain a pre-treatment level of inflammation; detecting inflammation in the subject according to the method described above after the therapeutic treatment to obtain a post-treatment level of inflammation; and comparing the pre-treatment and post-treatment levels of inflammation to determine the effect of the treatment on inflammation.

The method can further comprise determining a plurality of post-treatment levels of inflammation, each of which can be obtained at spaced apart time intervals post-treatment, to monitor the effect of the treatment over time.

The treatment can be determined to be successful if the post-treatment level of inflammation is lower than the pre-treatment level of inflammation, or if the post-treatment level of inflammation is higher than the pre-treatment level of inflammation but lower than would be expected had the treatment had not been performed. This aspect of the invention can be useful for monitoring regression, progression or treatment of a disease involving inflammation associated with upregulated amyloid and assessing the effect of therapeutic agents and treatment regimens on the disease. The therapeutic treatment can be any suitable treatment appropriate for the disease. In some embodiments in which the subject suffers from inflammation resulting from cancer, the therapeutic treatment may be radiation therapy, chemotherapy, immunotherapy, targeted therapy, hormone therapy, or stem cell transplant.

In some embodiments, the level of inflammation can be scored on a scale and given a qualitative value. In alternate embodiments, the level of inflammation can be assigned a quantitative value based on a quantity of amyloid in the subject's blood, typically a concentration, a concentration range, or a rate of amyloid formation. In some embodiments, an inflammation scale can be a scale of different stages of cancer, such as stages 0 to 4 cancer to which different levels of amyloid can be assigned.

Importantly, the method of the present invention makes use of a blood test rather than a biopsy to determine inflammation. This permits the risks, discomfort and inconvenience associated with biopsies to be circumvented. The present invention is also less expensive, faster and has a higher degree of sensitivity than existing methods used to detect inflammation and associated diseases. Furthermore, the use of fibrin(ogen) amyloid as a biomarker to detect early stage inflammation enables sensitive, early diagnosis of a number of potentially life threatening inflammatory diseases, thereby increasing the prospects of successful treatment.

The invention will now be described in further detail by the following non-limiting examples.

EXAMPLES

Example 1

Twenty healthy whole blood (WB) samples and twenty amyloidogenic blood samples with low grade inflammation were prepared in citrate tubes. Platelet poor plasma (PPP) was used for confocal and super-resolution analysis. Platelet poor plasma (PPP) was prepared by centrifuging WB for 15 minutes at 3000×g. One of three fluorescent markers, Thioflavin T (ThT), Amytracker®0480 or Amytracker®680, was added to the PPP to detect amyloid formation. The tubes were incubated for 30 minutes with ThT at a final concentration of 5 µM and Amytracker®480 and 680 (0.1 µL into 100 µL PPP).

Clots were allowed to form and were viewed under confocal microscope. Before viewing clots on the confocal microscope, thrombin was added in the ratio 1:2, (5 µL thrombin: 10 µL PPP) and extensive fibrin networks, created. Thrombin was provided by the South African National Blood Service, and the thrombin solution was at a concentration of 20 U/ml and made up in a biological buffer containing 0.2% human serum albumin. A coverslip was placed over the prepared clot, and samples were viewed using a Zeiss LSM 510 META confocal microscope with a Plan-Apochromat 63×/1.4 Oil DIC objective. For ThT, the excitation laser used was 488 nm and emission measured at 508 to 570 nm, for Amytracker® 480 the 405 nm laser was used with emission measured at 478 to 539 nm, and for Amytracker 680 the 561 nm laser was used for excitation with emission measured at 597 to 695 nm. A selection of micrographs of the prepared clots was captured. Fluorescent signals of each of the three fluorescent markers were captured as a composite.czi file in the Zeiss ZEN software, and ImageJ (FIJI) was used to split the channels. Variance between (black) background and fluorescent pixels (binary comparison) for each of the three fluorescent markers was assessed using the histogram function in ImageJ(FIJI). The coefficient of variation (CV) (as SD/mean) was calculated as a metric to quantify and discriminate between clots of healthy naïve PPP and clots of the amyloidogenic blood. Sample analysis was performed with the Mann-Whitney U test, using the STATSDIRECT (version 2.8.0) software.

Confocal analysis of healthy clotted PPP, in the presence of ThT, Amytracker™ 480 and 680, showed occasional small patches of fluorescence (see FIGS. 1A to C). However, when amyloidogenic blood was treated with thrombin, fluorescence was considerably increased for all three markers (FIGS. 1D to F). This demonstrated binding of the markers to fibrin(ogen) amyloid and showed that amyloid formation could be detected.

Figure 2:
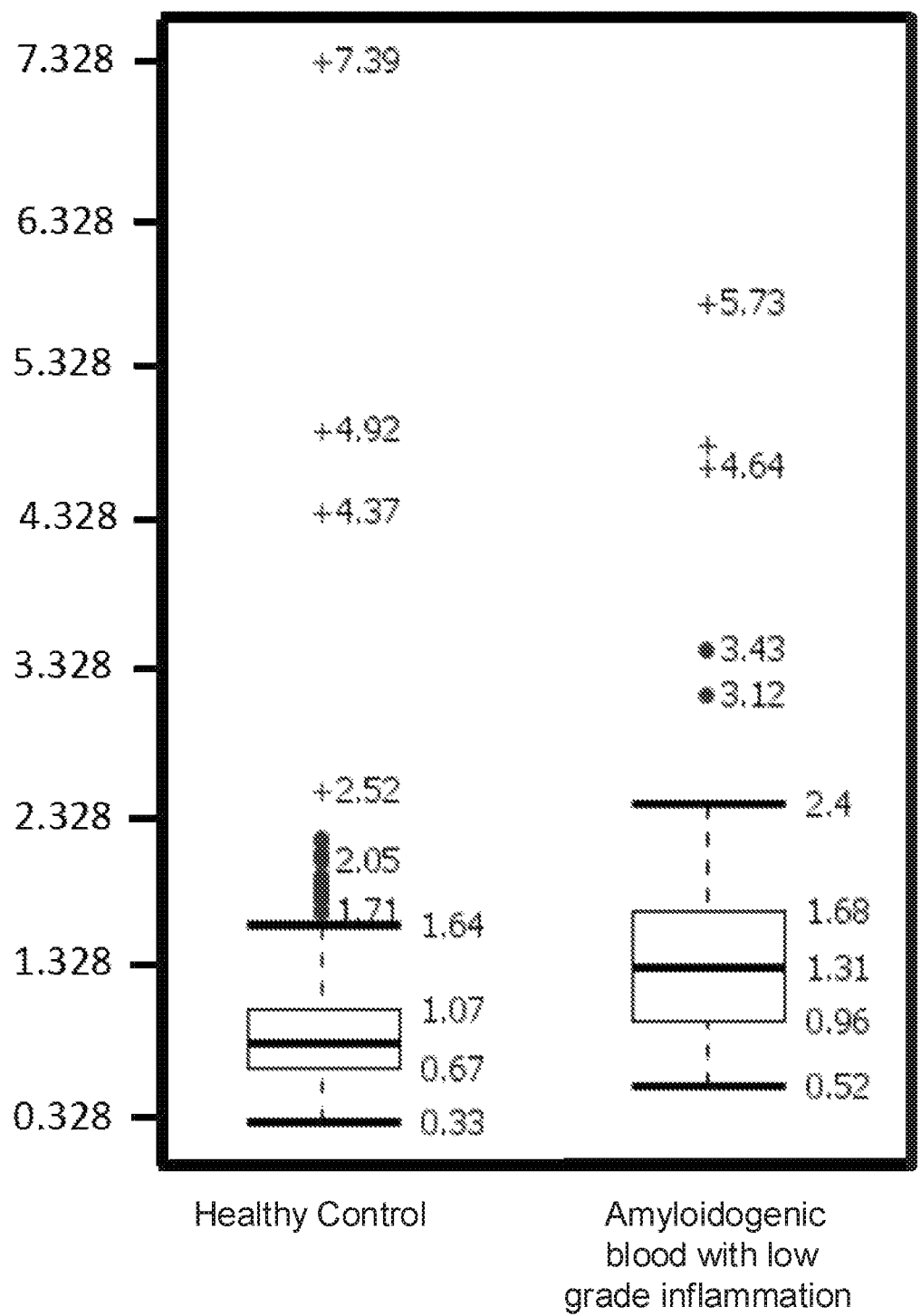
FIG. 2 is a boxplot of the distribution of the coefficients of variation (CV) for the pixel intensities in the confocal clot images from Amytracker® 480 (median coefficients of variation and STDs are reported above the plot). Data of the inflamed amyloidogenic blood differed significantly from that of the healthy control ($P<0.0001$).
Figure 3:
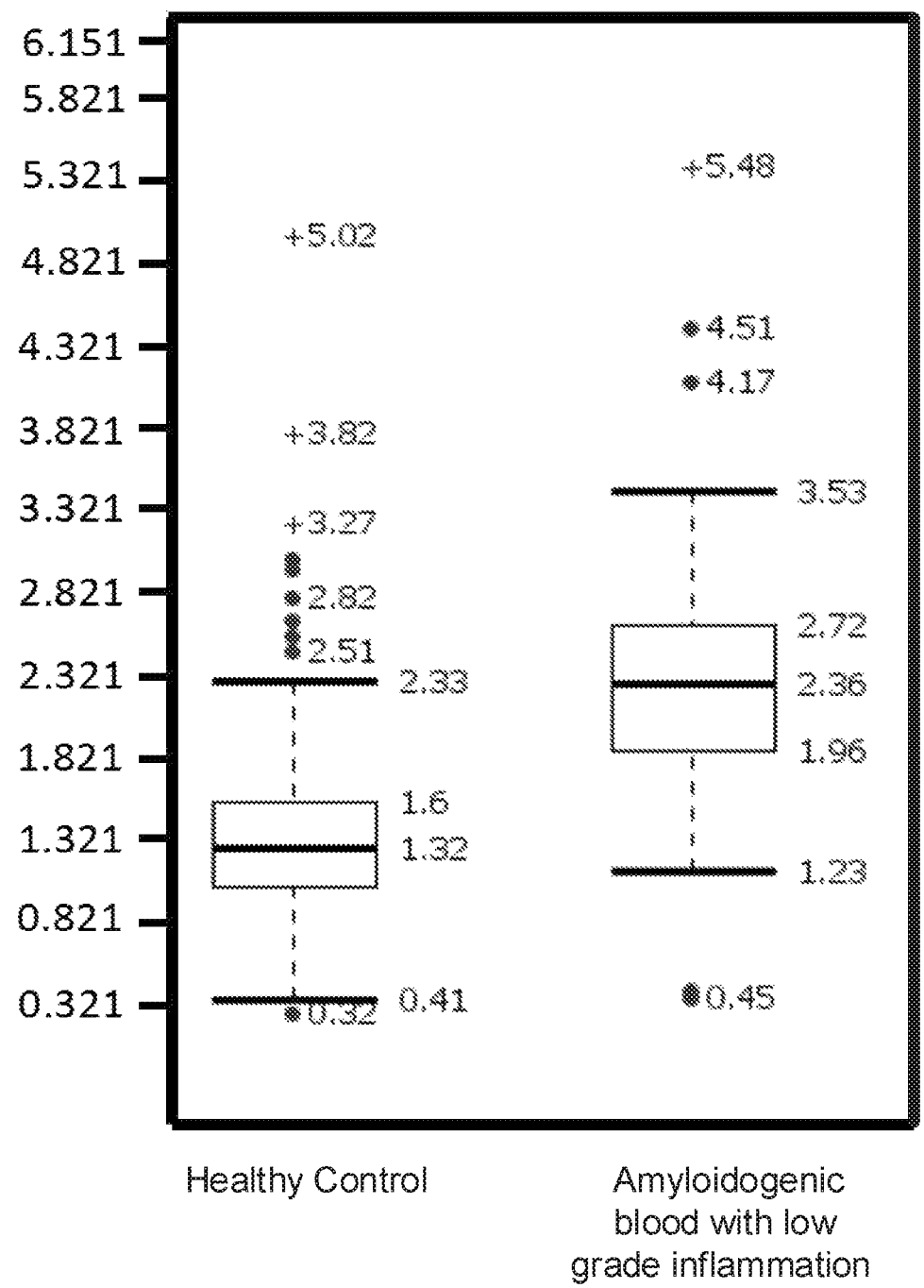
FIG. 3 is a boxplot of the distribution of the coefficients of variation (CV) for the pixel intensities in the confocal clot images from Amytracker® 680 (median coefficients of variation and STDs are reported above the plot). Data of the inflamed amyloidogenic blood differed significantly from that of the healthy control ($P<0.0001$).
Figure 4:
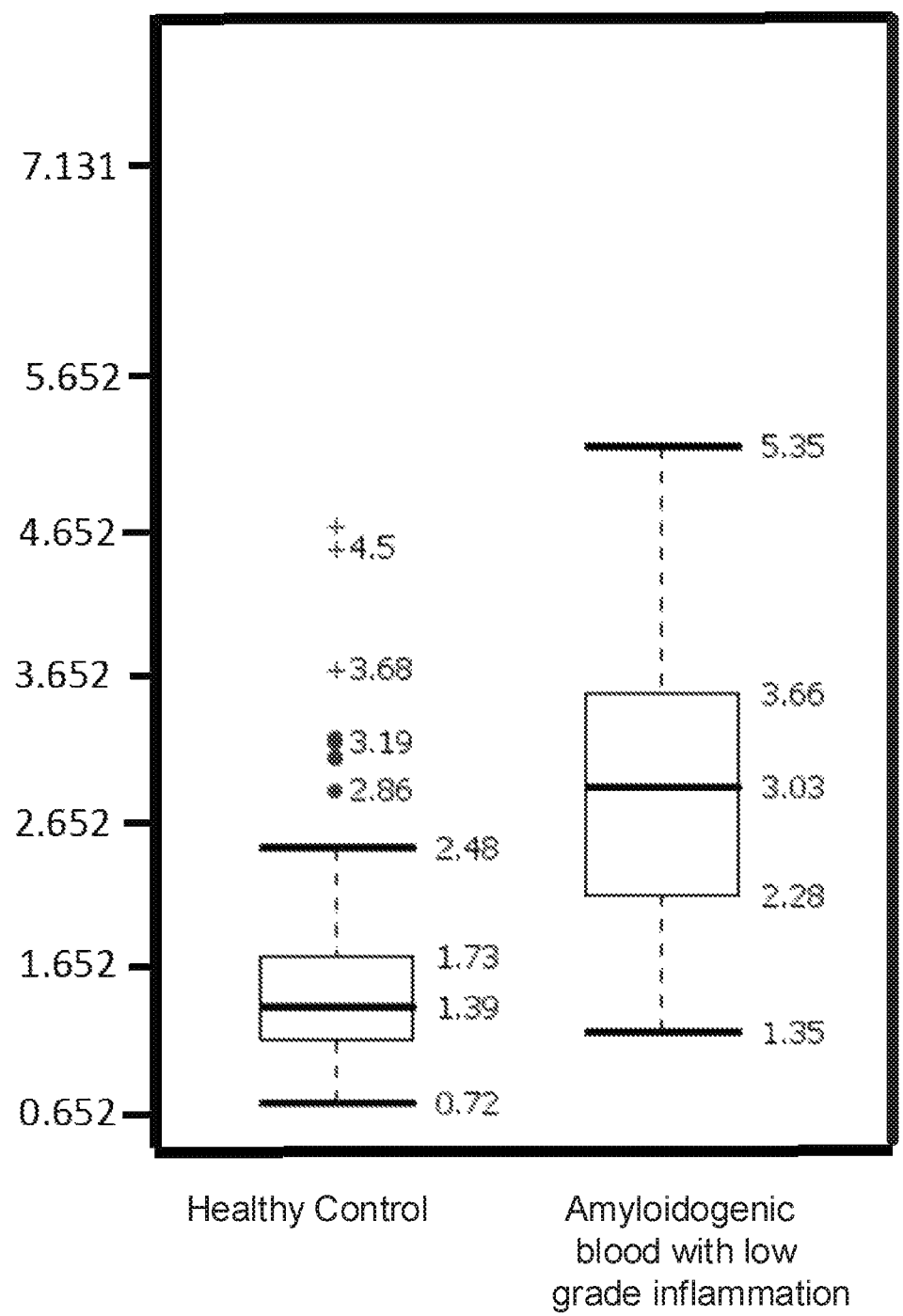
FIG. 4 is a boxplot of the distribution of the coefficients of variation (CV) for the pixel intensities in the confocal clot images from ThT (median coefficients of variation and STDs are reported above the plot). Data of the inflamed amyloidogenic blood differed significantly from that of the healthy control ($P<0.0001$).

Statistical (coefficient of variation, CV) data are plotted in FIGS. 2-4. These data provide quantified measures of fibrin (ogen) amyloid for the amyloidogenic blood having low grade inflammation. Data from the three different markers—Amytracker® 480 (FIG. 2), Amytracker® 680 (FIG. 3) and ThT (FIG. 4)—are shown.

A quantity of amyloid can be calculated by plotting the quantity of fluorescence on a standard curve and reading off the concentration of amyloid that corresponds to the quantity of fluorescence. The amyloid level can in turn be positively correlated to a level of inflammation by comparing the level of amyloid with a plurality of predetermined concentration ranges in which each concentration range has an associated level of inflammation. Furthermore, since SAA is an inducer of amyloid formation, a level of SAA in the blood can be determined based on the amount of amyloid present. A level of inflammation can then be assigned based on the level of SAA present in the blood.

Example 2

In order to demonstrate the detectability of cancer in a subject by measuring amyloid in a blood sample from the subject, naïve healthy cells from twenty-one individuals were contacted with metastatic human breast adenocarcinoma cell line MDA-MB-231 cells. The induction of healthy cells into a state of hypercoagulation, or amyloidogenesis, by cancer cells occurs in early stage cancer as the cancerous cells metastasize in the subject's blood and release elevated levels of SAA and other inflammogens. SAA is induces amyloid formation, which can be measured. By treating the blood with amyloid-binding fluorescent markers (and thrombin to induce fibrin formation) and measuring fluorescence, a quantity of amyloid structures present in fibrin (ogen) protein in the blood can be determined. A level of SAA present in the blood can be determined based on the quantity of amyloid present. A level of inflammation in the subject can be assigned based on the quantity of amyloid or SAA present, and cancer detected.

Amyloid formation was measured using confocal microscopy according to the following protocol: Naïve whole blood (WB), as well as WB exposed to human breast adenocarcinoma cell line MDA-MB-231 cells, were centrifuged to obtain platelet poor plasma (PPP). The PPP was incubated with a fluorescent marker, either ThT at a final concentration of 5 µM, or Amytracker™ 480 or Amytracker™ 680 (0.1 µL into 100 µL PPP) for 30-minutes. Before viewing clots on the confocal microscope, thrombin was added in the ratio 1:2, (5 µL thrombin: 10 µL PPP) to create extensive fibrin networks. Thrombin solution was at a concentration of 20 $U.mL^{-1}$ and made up in PBS containing 0.2% human serum albumin. A coverslip was placed over the prepared clot, and samples were viewed using a Zeiss LSM 780 with ELYRA PS1 confocal microscope with a Plan-Apochromat 63×/1.4 Oil DIC objective. For ThT, the 488 nm excitation laser was used, with emission measured at 508 to 570 nm; for Amytracker™ 480 the 405 nm excitation laser was used, with emission measured at 478 to 539 nm; and for Amytracker™ 680, the 561 nm excitation laser was used, with emission measured at 597 to 695 nm. A selection of micrographs of the prepared clots were captured. Gain settings were kept the same during all data capture and used for statistical analyses; however, brightness and contrast were slightly adjusted for figure preparation. The fluorescent signal of each of the three fluorescent markers was captured as a composite LSM file in the Zeiss ZEN software and then ImageJ (FIJI) was used to split and analyse the RGB channels.

The fluorescence of each stained clot was quantified by assessing the variance between the black background and the fluorescent pixels (binary comparison) for each of the three fluorescent markers in the clots. The histogram function in ImageJ (FIJI) was used to calculate the coefficient of variation (CV) (as SD/mean) of the histogram of different pixel intensities as a metric to quantify and discriminate between clots of healthy (age-controlled) naïve PPP and clots of cells induced into a state of hypercoagulation through contact with cancer cells. CVs were calculated from the data shown in each histogram. GraphPad Prism with Kruskal-Wallis posthoc test and Dunn's Multiple Comparison Test were used for the statistical analysis.

Figure 5:
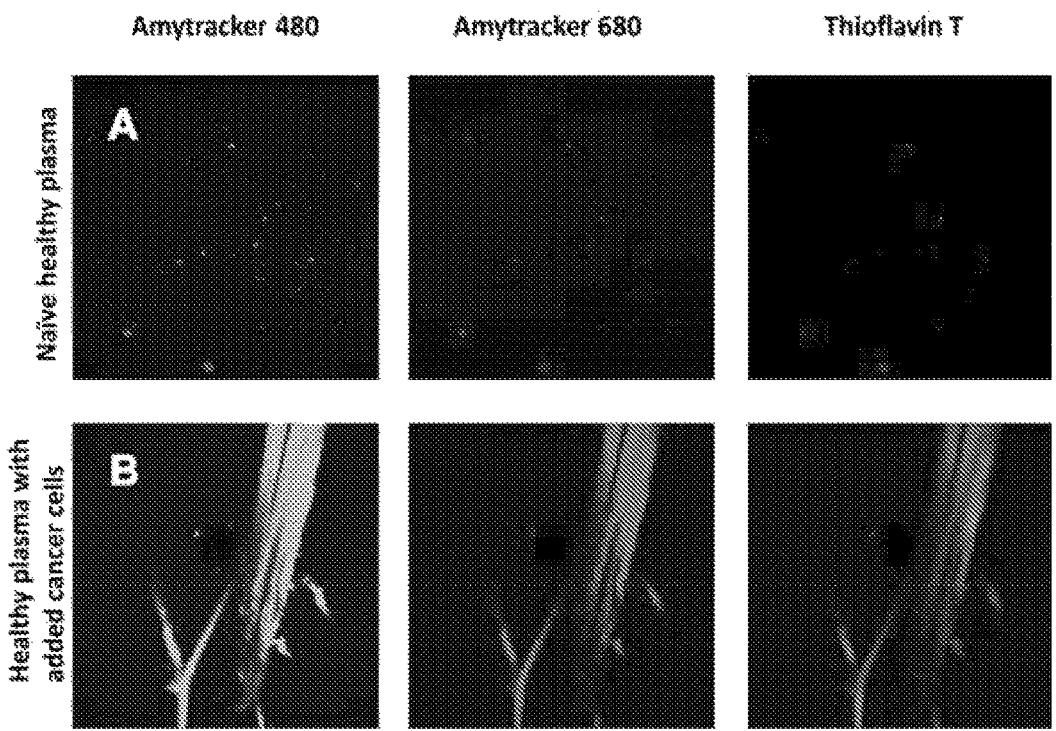
FIG. 5 shows representative confocal micrographs of plasma from a healthy individual with a BMI of 23 before and after exposure to cancer cells using 3 amyloid markers. A) Naïve healthy whole blood. B) Plasma from the same individual after exposure to cultured cancer cells.
Figure 6:
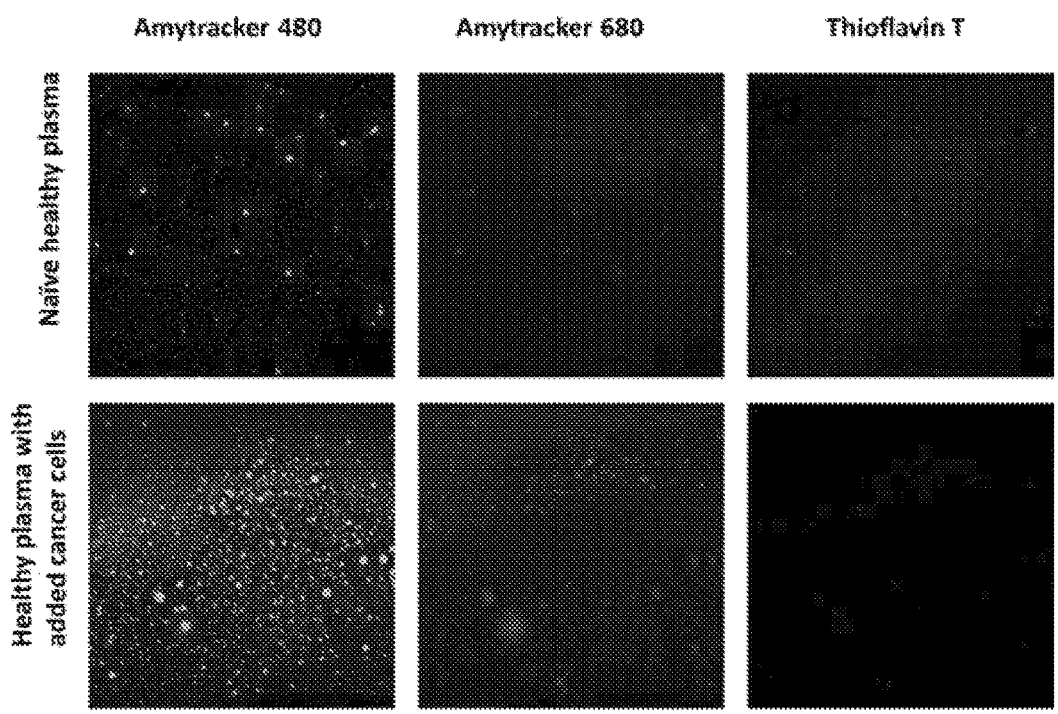
FIG. 6 shows representative confocal micrographs of plasma from a healthy individual with a BMI of 27.1 before and after exposure to cancer cells with 3 amyloid markers. A) Naïve healthy whole blood. B) Plasma from the same individual after exposure to cultured cancer cells.

FIGS. 5 and 6 show confocal micrographs of amyloid formation in plasma from representative normal body mass index (BMI) and high BMI individuals, before and after exposure to cancer cells. There were no significant differences between normal and high BMI individuals, although the high BMI individuals did show slightly increased amyloid formation when the micrographs were visually inspected. This is likely due to underlying systemic inflammation due to an increased body weight. The addition of cancer cells to plasma significantly increased the amyloid areas in the fibrin clot (this was noted from statistical analysis of all 3 fluorescent markers of amyloid structure). This was seen irrespective of the BMI of the individual.

Figure 7:
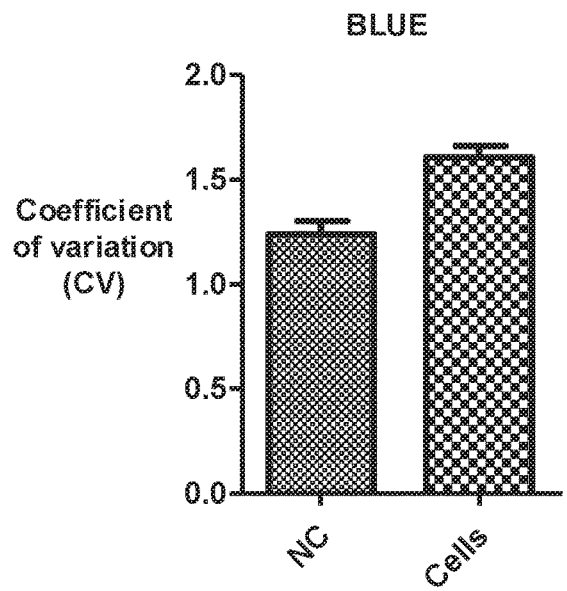
FIG. 7 is a graph of the coefficient of variation (CV) data obtained with Amytracker® 480 for naïve cells (NC) and cells contacted with cancer cells (Cells). Vertical bars indicate standard deviation.
Figure 8:
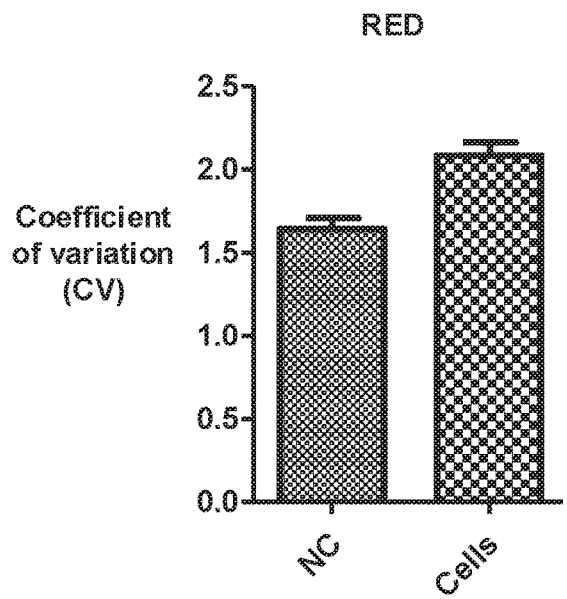
FIG. 8 is a graph of the coefficient of variation (CV) data obtained with Amytracker® 680 for naïve cells (NC) and cells contacted with cancer cells (Cells). Vertical bars indicate standard deviation.
Figure 9:
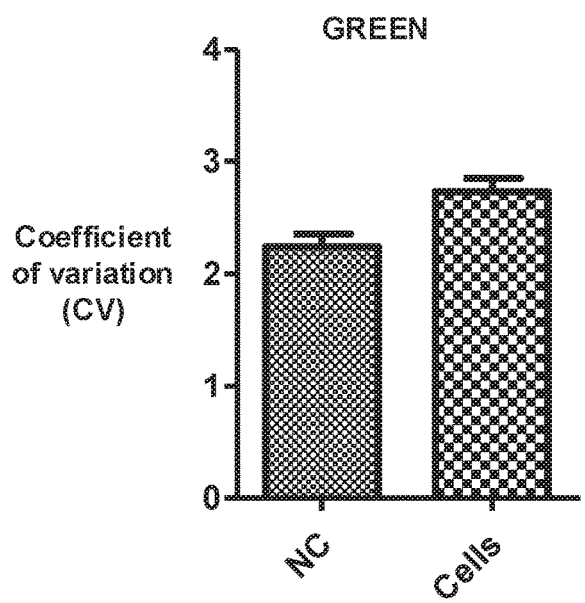
FIG. 9 is a graph of the coefficient of variation (CV) data obtained with ThT for naïve cells (NC) and cells contacted with cancer cells (Cells). Vertical bars indicate standard deviation.

Coefficient of variation (CV) data are provided in FIGS. 7-9 and were used to obtain the statistical data represented in Tables 2-4. Higher CV values indicate higher levels of amyloid formation. These data provide quantified measures of amyloidogenesis for the blood having low grade inflammation resulting from contact with cancer cells. Data from the three different markers—Amytracker® 480 (Table 2, FIG. 7), Amytracker® 680 (Table 3, FIG. 8) and ThT (Table 4, FIG. 9)—are shown.

TABLE 2

Amytracker 480 results of confocal parameters of naïve blood with and without treatment: NC = healthy naive control blood; Cells = NC blood with cancer cells added

| Amytracker 480 = Blue Kruskal-Wallis test | | | |
|---|---|---|---|
| P value | | P < 0.0001 | |
| Exact or approximate P value? | | Gaussian Approximation | |
| P value summary | | *** | |
| Do the medians vary signif. (P < 0.05) | | Yes | |
| Number of groups | | 4 | |
| Kruskal-Wallis statistic | | 46.33 | |
| Dunn's Multiple Comparison Test | Difference in rank sum | Significant? P < 0.05? | Summary |
| NC vs Cells | −78.60 | Yes | *** |

TABLE 3

Amytracker 680 results of confocal parameters of naïve blood with and without treatment: NC = healthy naive control blood; Cells = NC blood with cancer cells added

| Amytracker 680 = Red Kruskal-Wallis test | |
|---|---|
| P value | P < 0.0001 |
| Exact or approximate P value? | Gaussian Approximation |
| P value summary | *** |
| Do the medians vary signif. (P < 0.05) | Yes |

TABLE 3-continued

Amytracker 680 results of confocal parameters of naïve
blood with and without treatment: NC = healthy naive control
blood; Cells = NC blood with cancer cells added

| Number of groups | 4 |
| --- | --- |
| Kruskal-Wallis statistic | 34.77 |

| Dunn's Multiple Comparison Test | Difference in rank sum | Significant? P < 0.05? | Summary |
| --- | --- | --- | --- |
| NC vs Cells | −64.72 | Yes | *** |

TABLE 4

ThT results of confocal parameters of naïve blood
with and without treatment: NC = healthy naive control
blood; Cells = NC blood with cancer cells added

| ThT = Green Kruskal-Wallis test | |
| --- | --- |
| P value | 0.0002 |
| Exact or approximate P value? | Gaussian Approximation |
| P value summary | *** |
| Do the medians vary signif. (P < 0.05) | Yes |
| Number of groups | 4 |
| Kruskal-Wallis statistic | 20.02 |

| Dunn's Multiple Comparison Test | Difference in rank sum | Significant? P < 0.05? | Summary |
| --- | --- | --- | --- |
| NC vs Cells | −53.08 | Yes | ** |

The quantified fibrin(ogen) amyloid structures can be positively correlated to a level of inflammation by comparing the level of amyloid with a plurality of predetermined concentration ranges in which each concentration range has an associated level of inflammation. Where the level of inflammation falls within a predetermined range for cancer, cancer can be detected.

Throughout the specification unless the content requires otherwise the word 'comprise' or variations such as 'comprises' or 'comprising' will be understood to imply the inclusion of a stated integer or group of integers but not the exclusion of any other integer or group of integers.

The invention claimed is:

1. A method of detecting and treating inflammation in a subject, the inflammation indicating cancer, the method comprising the steps of:
   determining a quantity of amyloid present in fibrin clots in a blood sample obtained from the subject by contacting the blood sample with an amyloid-binding fluorescent marker and measuring fluorescence emitted upon binding of amyloid to the fluorescent marker;
   determining a concentration of serum amyloid A (SAA) in the blood sample, wherein the concentration of SAA is determined using an enzyme-linked immunosorbent assay (ELISA);
   determining inflammation in the subject if both the quantity of amyloid in the blood sample is greater than a threshold level, the threshold level being 2 times a predetermined blood level of amyloid associated with a healthy subject without inflammation and the concentration of SAA is greater than 30 micrograms/ml; and
   administering an effective amount of a treatment for reducing the determined inflammation or for treating cancer to the subject, wherein the treatment is chemotherapy or immunotherapy.

2. The method as claimed in claim 1, comprising assigning a quantity of amyloid based on the measured fluorescence.

3. The method as claimed in claim 2, wherein assigning the quantity of amyloid comprises comparing the measured fluorescence to a reference.

4. The method as claimed in claim 3, comprising selecting the reference from the group consisting of one or more predetermined values, a chart and a graph.

5. The method as claimed in claim 1, which comprises contacting the blood sample with thrombin so as to form fibrin clots, prior to the step of determining the quantity of amyloid.

6. The method as claimed in claim 1, wherein early-stage inflammation is detectable.

7. The method as claimed in claim 6, wherein inflammation is detectable in subjects who have no symptoms of inflammation or disease.

8. The method as claimed in claim 1, wherein the cancer is stage 0 or stage 1 cancer.

9. The method as claimed in claim 1, wherein the treatment is chemotherapy.

10. The method as claimed in claim 1, wherein the concentration of SAA is determined either prior to or after the quantity of amyloid being determined.

11. The method as claimed in claim 1, wherein the concentration of SAA is determined prior to the quantity of amyloid being determined.

12. The method as claimed in claim 1, wherein the concentration of SAA is determined after the quantity of amyloid has been determined.

13. The method as claimed in claim 1, wherein the treatment is immunotherapy.

* * * * *